(12) United States Patent
Jinton et al.

(10) Patent No.: US 10,750,298 B2
(45) Date of Patent: Aug. 18, 2020

(54) BONE ANCHOR FIXTURE FOR A MEDICAL PROSTHESIS

(71) Applicants: Lars Jinton, Mölndal (SE); Erik Holgersson, Gothenburg (SE); Peter Elmberg, Kållered (SE)

(72) Inventors: Lars Jinton, Mölndal (SE); Erik Holgersson, Gothenburg (SE); Peter Elmberg, Kållered (SE)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 15/831,325

(22) Filed: Dec. 4, 2017

(65) Prior Publication Data

US 2018/0220246 A1 Aug. 2, 2018

Related U.S. Application Data

(63) Continuation of application No. 14/922,604, filed on Oct. 26, 2015, now Pat. No. 9,838,807, which is a
(Continued)

(51) Int. Cl.
*H04R 25/00* (2006.01)
*A61C 8/00* (2006.01)
*A61B 17/86* (2006.01)

(52) U.S. Cl.
CPC ......... *H04R 25/606* (2013.01); *A61B 17/863* (2013.01); *A61B 17/8615* (2013.01);
(Continued)

(58) Field of Classification Search
CPC .. H04R 25/606; A61B 17/8615; A61B 17/863
See application file for complete search history.

(56) References Cited

U.S. PATENT DOCUMENTS 2,016,610 A 10/1935 Moeller
2,347,567 A 4/1944 Kresse
(Continued)

FOREIGN PATENT DOCUMENTS

EP 0996391 B1 2/2004
KR 20120000235 A 1/2012
(Continued)

OTHER PUBLICATIONS

Extended European Search Report for European Application No. 087821575 dated Jan. 2, 2013.
(Continued)

*Primary Examiner* — Christian A Sevilla
(74) *Attorney, Agent, or Firm* — Pilloff Passino & Cosenza LLP; Martin J. Cosenza

(57) ABSTRACT

A screw-shaped anchoring fixture for anchoring a prosthesis in the skull bone. The anchoring fixture comprises a main body configured to be implanted into the bone and a flange configured to function as a stop to prevent the main body from completely penetrating through the bone. The main body comprises a distal tapered apical portion, a first portion, and a second portion. The inner diameter of the second portion is greater than the inner diameter of the first portion. The method for inserting the anchoring fixture includes providing the anchoring fixture, drilling a hole, and inserting the anchoring fixture into the hole until the flange contacts the skull bone, wherein the hole has a diameter that is greater than the inner diameter of the first portion and less than the outer diameter of the second portion.

64 Claims, 7 Drawing Sheets

Related U.S. Application Data continuation of application No. 12/177,083, filed on Jul. 21, 2008, now Pat. No. 9,173,042.

(60) Provisional application No. 60/951,169, filed on Jul. 20, 2007, provisional application No. 60/951,163, filed on Jul. 20, 2007.

(52) U.S. Cl.
CPC .......... *A61C 8/0025* (2013.01); *A61C 8/0066* (2013.01); *A61C 8/0069* (2013.01); *H04R 2460/13* (2013.01)

(56) References Cited

U.S. PATENT DOCUMENTS

| | | | |
|---|---|---|---|
| 4,025,964 | A | 5/1977 | Owens |
| 4,498,461 | A | 2/1985 | Hakansson |
| D294,295 | S | 2/1988 | Branemark |
| 4,738,623 | A | 4/1988 | Driskell |
| 4,904,233 | A | 2/1990 | Hakansson et al. |
| 4,917,555 | A | 4/1990 | Taubert |
| 4,936,317 | A | 6/1990 | MacGregor |
| 4,998,461 | A | 3/1991 | Ishiwata et al. |
| 5,019,078 | A | 5/1991 | Perren et al. |
| 5,135,395 | A | 8/1992 | Marlin |
| 5,269,685 | A | 12/1993 | Jornéus et al. |
| 5,588,883 | A | 12/1996 | Hattori |
| 5,653,710 | A | 8/1997 | Harle |
| 5,720,766 | A | 2/1998 | Zang et al. |
| 5,735,790 | A | 4/1998 | Hakansson et al. |
| 5,769,630 | A | 6/1998 | Hoffman |
| 5,833,463 | A | 11/1998 | Hurson |
| 5,885,079 | A | 3/1999 | Niznick |
| 5,961,329 | A | 10/1999 | Stucki-McCormick |
| 6,030,162 | A | 2/2000 | Huebner |
| 6,086,303 | A | 7/2000 | Fluckiger |
| 6,183,255 | B1 | 2/2001 | Oshida |
| 6,468,277 | B1 | 10/2002 | Justin et al. |
| 6,474,991 | B1 | 11/2002 | Hansson |
| 6,604,945 | B1 | 8/2003 | Jones |
| 6,643,378 | B2 | 11/2003 | Schumaier |
| 6,669,701 | B2 | 12/2003 | Stiener et al. |
| 6,840,919 | B1 | 1/2005 | Hakansson |
| 6,896,517 | B1 | 5/2005 | Bjorn et al. |
| 6,953,463 | B2 | 10/2005 | West, Jr. |
| 6,981,873 | B2 | 1/2006 | Choi et al. |
| 7,065,223 | B2 | 6/2006 | Westerkull |
| 7,074,222 | B2 | 7/2006 | Westerkull |
| 7,116,794 | B2 | 10/2006 | Westerkull |
| 7,806,693 | B2 | 10/2010 | Hurson |
| D634,186 | S | 3/2011 | Kemper |
| 8,016,593 | B2 | 9/2011 | Hall |
| 8,170,252 | B2 | 5/2012 | Parker et al. |
| 8,377,106 | B2 | 2/2013 | Branemark et al. |
| 9,931,184 | B2 | 4/2018 | Hall |
| 2003/0176866 | A1 | 9/2003 | Westerkull |
| 2004/0032962 | A1 | 2/2004 | Westerkull |
| 2004/0152047 | A1 | 8/2004 | Odrich et al. |
| 2004/0210103 | A1 | 10/2004 | Westerkull |
| 2004/0228705 | A1 | 11/2004 | Baer et al. |
| 2005/0106534 | A1 | 5/2005 | Gahlert |
| 2005/0153261 | A1 | 7/2005 | Chang |
| 2005/0248158 | A1 | 11/2005 | Westerkull |
| 2005/0249366 | A1 | 11/2005 | Westerkull |
| 2005/0250074 | A1 | 11/2005 | Lang et al. |
| 2005/0287497 | A1 | 12/2005 | Carter |
| 2006/0050913 | A1 | 3/2006 | Westerkull |
| 2006/0056649 | A1 | 3/2006 | Schumaier |
| 2006/0093175 | A1 | 5/2006 | Westerkull |
| 2006/0126874 | A1 | 6/2006 | Westerkull |
| 2006/0172257 | A1 | 8/2006 | Niznick |
| 2006/0195099 | A1 | 8/2006 | Bottlang |
| 2006/0211910 | A1 | 9/2006 | Westerkull |
| 2007/0009853 | A1 | 1/2007 | Pitulia |
| 2007/0053536 | A1 | 3/2007 | Westerkull |
| 2007/0059666 | A1 | 3/2007 | Zickman et al. |
| 2007/0147973 | A1 | 6/2007 | Laan |
| 2008/0032264 | A1 | 2/2008 | Hall |
| 2009/0023109 | A1 | 1/2009 | Jinton et al. |
| 2009/0082817 | A1 | 3/2009 | Jinton et al. |
| 2010/0240010 | A1 | 9/2010 | Holmstrom |
| 2010/0249784 | A1 | 9/2010 | Andersson |
| 2010/0286776 | A1 | 11/2010 | Andersson |
| 2011/0195380 | A1 | 8/2011 | Giomo |
| 2012/0143251 | A1 | 6/2012 | Green et al. |
| 2015/0215696 | A1 | 7/2015 | Bjorn et al. |

FOREIGN PATENT DOCUMENTS

| | | |
|---|---|---|
| SE | 531177 C2 | 1/2009 |
| WO | 9205745 A1 | 4/1992 |
| WO | 9619950 A1 | 7/1996 |
| WO | 9855049 A1 | 12/1998 |
| WO | 9923971 A1 | 5/1999 |
| WO | 0193634 A1 | 12/2001 |
| WO | 0193645 A1 | 12/2001 |
| WO | 0209622 A1 | 2/2002 |
| WO | 2004012622 A1 | 2/2004 |
| WO | 2004045432 A1 | 6/2004 |
| WO | 2004058091 A1 | 7/2004 |
| WO | 2004093401 A1 | 10/2004 |
| WO | 2004098442 A1 | 11/2004 |
| WO | 2004105650 A1 | 12/2004 |
| WO | 2005000391 A1 | 1/2005 |
| WO | 2006052527 A2 | 5/2006 |
| WO | 2006065205 A1 | 6/2006 |
| WO | 2009015102 A1 | 1/2009 |
| WO | 2009015103 A1 | 1/2009 |

OTHER PUBLICATIONS

Extended European Search Report for European Application No. 08782159.1 dated Jan. 3, 2013.
Sjostrom et al., "Monitoring of implant stability in grafted bone using resonance frequency analysis—A clinical study from implant placement to 6 months of loading", Jan. 2005, pp. 45-51, vol. 34, issue 1.
http://www.merriam-webster.com/dictionary/tapered, Retrieved Apr. 10, 2012.
http://www.merriam-webster.com/dictionary/apical, Retrieved Apr. 10, 2012.
http://www.merriam-webster.com/dictionary/portion, Retrieved Apr. 10, 2012.
Written Opinion for PCT/US2008/070679, dated Oct. 27, 2008.
International Preliminary Report on Patentability for PCT/US2008/070681, dated Aug. 21, 2009.
Written Opinion for PCT/US2008/070681, dated Dec. 15, 2008.
Mats Thomsson et al., "A retrospective case series evaluating Branemark BioHelix implants placed in a specialist private practice following 'conventional' procedures. One-year results after placement," Eur J Oral Implantol., Oct. 2008, pp. 229-234, vol. 1, No. 3.
Oticon Medical AB et al., "Defendants' Invalidity Contentions," U.S. District Court for the District of New Jersey, Case No. 3:18-cv-06684, filed Oct. 9, 2018.
Cochlear Ltd., "Cochlear Ltd.'s Responses to Invalidity Contentions," U.S. District Court for the District of New Jersey, Case No. 3:18-cv-06684, filed Oct. 15, 2018.
Cochlear Ltd., "Plaintiff Cochlear Ltd.'s Opening Brief Regarding Claim Construction," U.S. District Court for the District of New Jersey, Case No. 3:18-cv-06684, filed Jan. 18, 2019.
Cochlear Ltd., "Declaration of Mark E. Rentschler, Ph.D. In Support of Plaintiff's Opening Brief Regarding Claim Construction," U.S. District Court for the District of New Jersey, Case No. 3:18cv-06684, filed Jan. 18, 2019.
Oticon Medical AB et al., "Oticon Medical's Opening Claim Construction Brief," U.S. District Court for the District of New Jersey, Case No. 3:18-cv-06684, filed Jan. 18, 2019.
Oticon Medical AB et al., "Expert Declaration of Dr. Wilson Hayes in Support of Oticon Medical AB and Oticon Medical LLC's Claim

(56) References Cited

OTHER PUBLICATIONS

Construction Brief," U.S. District Court for the District of New Jersey, Case No. 3:18-cv-06684, filed Jan. 18, 2019.
Oticon Medical AB et al., "Oticon Medical's Rebuttal Claim Construction Brief," U.S. District Court for the District of New Jersey, Case No. 3:18-cv-06684, filed Mar. 1, 2019.
Cochlear Ltd., "Plaintiff Cochlear Ltd.'s Responsive Brief Regarding Claim Construction," U.S. District Court for the District of New Jersey, Case No. 3:18-cv-06684, filed Mar. 1, 2019.
Cochlear Ltd., "Supplemental Declaration of Mark. E. Rentschler, Ph.D. In Support of Plaintiff Cochlear Ltd.'s Claim Constructions," U.S. District Court for the District of New Jersey, Case No. 3:18-cv-06684, filed Mar. 1, 2019.
Oticon Medical AB et al., "Oticon Medical's Supplemental Submission on Claim Construction," U.S. District Court for the District of New Jersey, Case No. 3:18-cv-06684, filed Jul. 10, 2019.
Cochlear Ltd., "Plaintiff Cochlear Ltd.'s Supplemental Brief Regarding Claim Construction," U.S. District Court for the District of New Jersey, Case No. 3:18-cv-06684, filed Jul. 10, 2019.
Cochlear Ltd., "Cochlear Ltd.'s Amended Responses to Invalidity Contentions," U.S. District court for the District of New Jersey, Case No. 3:18-cv-06684, filed Aug. 9, 2019.
Oticon Medical AB et al., "Petition for Inter Partes Review of of U.S. Pat. No. 9,838,807," IPR2019-00975, filed Apr. 15, 2019.
E.M. Lillie et al., "Evaluation of Skull Cortical Thickness Changes With Age and Sex From Computed Tomography Scans," Journal of Bone and Mineral Research, vol. 31(2), pp. 299-307 (Feb. 2016).
J.J. Wazen et al., "Long-Term Results With the Titanium Bone-Anchored Hearing Aid: The U.S. Experience," The American Journal of Otology, vol. 19, pp. 737-741 (1998).
M. Chasin et al., "Current Trends in Implantable Hearing Aids," Trends in Amplification, vol. 2, No. 3, pp. 84-107 (1997).
A. Tjellström et al., "Osseointegrated Titanium Implants in the Temporal Bone," The American Journal of Otology, vol. 2, No. 4, pp. 304-310 (1998).
L. Rasmusson et al., "Effects of Implant Design and Surface on Bone Regeneration and Implant Stability: An Experimental Study in the Dog Mandible," Clinical Implant Dentistry and Related Research, vol. 3, No. 1, pp. 2-8 (2001).
Cochlear Limited, "Patent Owner's Preliminary Response," IPR2019-00975, filed Jul. 20, 2019.
Christine A. den Besten et al., "Stability, Survival, and Tolerability of an Auditory Osseointegrated Implant for Bone Conduction Hearing: Long-Term Follow-Up of a Randomized Controlled Trial," Otology & Neurotology, vol. 37, pp. 1077-1083 (2016).
Soren Foghsgaard et al., "A New Wide-Diameter Bone-Anchored Hearing Implant—Prospective 1-Year Data on Complications, Implant Stability, and Survival," Otology & Neurotology, vol. 35, pp. 1238-1241 (2014).
Rik C. Nelissen et al., "Stability, Survival, and Tolerability of a 4.5-mm-wide Bone-anchored Hearing Implant: 6-month Data from a Randomized Controlled Clinical Trial," Eur. Arch. Otorhinolaryngol., DOI 10.1007/s00405-015-3593-x (2015).
Cochlear Limited, "Patent Owner's Updated Exhibit List," IPR2019-00975, filed Jan. 13, 2020.
Cochlear Limited, "Patent Owner's Updated Exhibit List," IPR2019-00975, filed Jan. 23, 2020.
"Joint Redacted Patent Owner's Response," IPR2019-00975, filed Jan. 23, 2020.

BONE ANCHOR FIXTURE FOR A MEDICAL PROSTHESIS

CROSS-REFERENCE TO RELATED APPLICATIONS

The present application is a Continuation application of U.S. patent application Ser. No. 14/922,604, filed Oct. 26, 2015, naming Lars Jinton as an inventor, which is a Continuation application of U.S. patent application Ser. No. 12/177,083, filed Jul. 21, 2008, now U.S. Pat. No. 9,173,042, which claims the benefit of U.S. Provisional Application No. 60/951,163, filed Jul. 20, 2007, and U.S. Provisional Application No. 60/951,169, filed Jul. 20, 2007. The entire contents of these applications are incorporated herein by reference in their entirety.

BACKGROUND

Field of the Invention

The present invention relates generally to hearing devices and, more particularly, to anchoring elements for bone anchored hearing devices.

Related Art

For persons who cannot benefit from traditional, air conduction hearing aids there are other types of hearing aids on the market commonly referred to as bone anchored hearing aids. Bone anchored hearing aids mechanically transmit sound information to a person's inner ear via the skull bone by means of a vibrator. Such hearing aid devices are typically connected to a percutaneous implant in the form of a titanium screw implanted in the skull bone behind the external ear so that sound is transmitted via the skull bone to the cochlea (inner ear). This enables the hearing aid to be effective regardless of whether there is disease or damage in the middle ear. Moreover, penetration of the skin makes the vibratory transmission very efficient.

Bone anchored hearing aids were initially developed to rehabilitate certain types of hearing-impaired patients. They may also be utilized for other indications such as stuttering and for certain non-medical applications. A bone anchored hearing aid may be connected to an implant by means of a bayonet coupling, a snap-in coupling, a magnetic coupling or the like. One example of this type of hearing aid device is the BAHA® bone anchored hearing aid, described in U.S. Pat. No. 4,498,461 and commercially available from Cochlear Bone Anchored Solutions AB (previously Entific Medical Systems AB) in Goteborg, Sweden.

The implant connecting the hearing aid to the skull generally comprises two components: a bone attachment piece that is attached or implanted directly into the skull bone and a skin penetrating piece coupled to the bone attachment piece. The reason for this two-piece design is that installation of the implant is occasionally performed in two steps. In the first step, the bone attachment piece is installed and the surrounding issue is allowed to heal for a period of time that may last up to a few months. In the second step, the skin penetrating piece is coupled to the bone attachment piece. In the event that the skin penetrating piece becomes damaged, it may be replaced without removing the anchoring fixture from the skull. Moreover, the hearing aid may be changed or upgraded if necessary, without removing the bone attachment piece from the skull.

Although conventional fixtures normally provide a certain degree of osseo-integration, a more effective integration between the implant screw and the skull bone is desired, for example, for patients having impaired bone quality. Moreover, loading of the implant at an earlier stage would also be desired.

A well known problem with conventional percutaneous implants is the infections and inflammation at the skin-implant interface resulting from bacterial colonization in the region surrounding the interface.

SUMMARY

In one embodiment, an anchoring fixture for anchoring a prosthesis to a skull bone is disclosed. The anchoring fixture comprises a main body configured to be implanted into the skull bone. The main body further comprises a distal tapered apical portion and a first portion adjacent to the distal tapered apical portion. The main body also comprises a second portion adjacent to the first portion. The first portion has a first inner diameter and the second portion has a second inner diameter that is greater than the first inner diameter. This configuration provides compression in the radial direction on the skull bone to improve the initial stability of the anchoring fixture.

In another embodiment, an anchoring fixture for anchoring a prosthesis to a skull bone is disclosed. The anchoring fixture comprises a main body configured to be implanted into the skull bone and a flange. The main body further comprises a distal tapered apical portion and a first threaded portion having a first diameter adjacent to the distal apical portion and an adjacent second threaded portion having a second diameter. The second diameter is greater than the first diameter. The flange is adjacent to the second threaded portion, the flange comprising a planar bottom surface adapted to rest on top of the skull bone when the main body is implanted into the skull bone.

In yet another embodiment, an anchoring fixture for anchoring a prosthesis to a skull bone is disclosed. The anchoring fixture comprises an implantation means for securing the anchoring fixture onto the skull bone without completely penetrating through the skull bone. The implantation means comprises a compression means for exerting a compression onto the skull bone in a radial direction to stabilize the fixture in the skull bone.

In a further embodiment, a method for installing the anchoring fixture into a skull bone is disclosed. The method comprises providing an anchoring fixture, drilling a hole into the skull bone and inserting the anchoring fixture in the hole until the flange contacts the skull bone, wherein the hole has a diameter that is greater than the inner diameter of the first portion and less than the outer diameter of the second portion. In one aspect of the embodiment, the inserting step comprises screwing the anchoring fixture into the skull bone.

In one aspect, an anchoring fixture for permanent anchorage of a prostheses in the skull bone is disclosed, the fixture comprising: a main body configured to be implanted into the bone and having a tapered apical portion and a first substantially cylindrical portion with a screw thread having a first inner diameter, wherein said main body further comprises a second, substantially cylindrical portion adjacent to a bottom surface of the flange having an inner diameter exceeding an inner diameter of said screw thread.

In one aspect, a coupling apparatus for anchorage of a prosthesis to a patient's skull bone, is disclosed comprising: an elongate anchoring fixture comprising an external screw thread for penetrating the bone, and a flange that abuts the bone when the fixture is implanted, wherein a proximate end of the fixture has an open cavity with a tapered interior contour; and a skin-penetrating abutment, detachably connectable to said fixture, comprising a substantially conical exterior surface with a wider proximate region and a narrower distal region having a tapered exterior contour that fits within said tapered interior contour of said open cavity.

BRIEF DESCRIPTION OF THE DRAWINGS

Embodiments of the present invention are described herein with reference to the accompanying drawings, in which.

Like numerals refer to like parts throughout the several views of the drawings.

DETAILED DESCRIPTION OF THE INVENTION

Aspects of the various embodiments disclosed herein are generally directed to providing screw-shaped anchoring fixtures configured to be anchored in the comparatively thin skull bone and having a certain compressive ability in the radial direction to improve the initial stability of the fixture.

Aspects of the present invention are also generally directed to a bone anchored coupling apparatus in which the percutaneous surfaces of an implanted fixture component and an associated abutment component are configured so as to reduce the risk for micro-gaps and unwanted micro-leakage, preferably regardless of any imperfectness of the mating surfaces and any incorrect tightening torques.

In one embodiment, the anchoring fixture has a main body configured to be inserted in the skull bone and a flange configured to prevent the fixture from completely penetrating through the skull bone. The main body comprises a first and second substantially cylindrical portion. The first portion comprises a screw thread having a first inner diameter and the second portion is adjacent to the flange and has a second inner diameter that is greater than the first inner diameter. Preferably, the second portion has at least one groove extending around the periphery of the cylindrical portion. The groove may have a bottom diameter exceeding the first inner diameter of the screw thread. Preferably, the groove forms a second screw thread having an inner diameter exceeding the inner diameter of the first, main screw thread. The surface of at least the first portion of the main body may be modified to increase the surface roughness.

In another embodiment, a method for inserting the anchoring fixture is disclosed. In accordance with one aspect of this embodiment, a drill may be used to drill a hole in the skull bone before installing the anchoring fixture. The drill creates a hole in the skull bone having a diameter which is larger than the inner diameter of the screw thread of the first cylindrical portion, but less than the outer diameter of the second cylindrical portion. When the fixture is inserted into the drilled hole, the wider second portion of the fixture, i.e. the portion next to the flange, provides a certain compression to the bone, specifically the cortical bone, in the radial direction of the hole.

Figure 8:
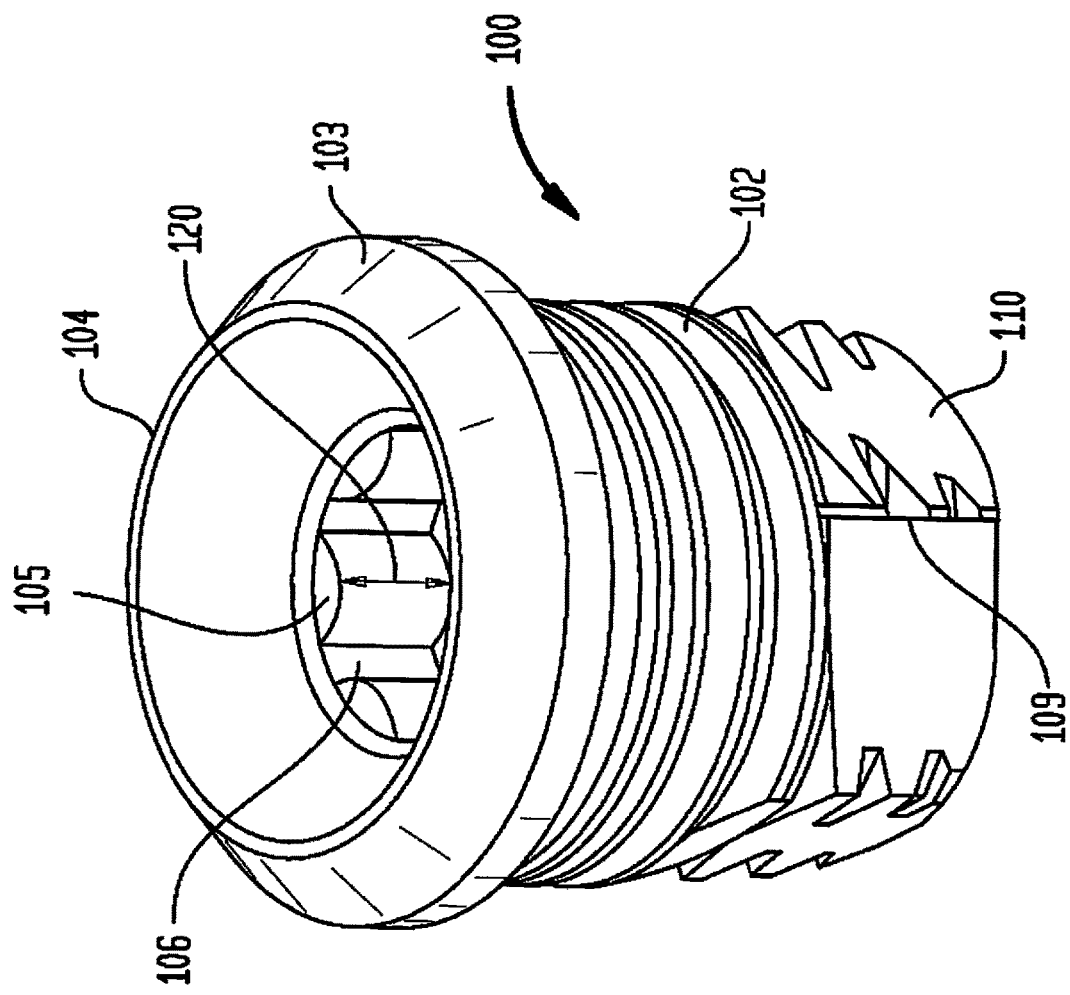
FIG. 8 is a perspective view of an anchoring element in accordance with one embodiment of the anchoring fixture.

Embodiments of the bone anchored coupling apparatus will be described below with reference to the accompanying drawings. FIG. 8 illustrates an example of a screw-shaped anchoring fixture 100 in accordance with one embodiment. Fixture 100 is preferably made of any biocompatible material that has a known ability to integrate with the surrounding bone tissue, a phenomenon commonly referred to as osseointegration. In one embodiment, fixture 100 is made of titanium. Fixture 100 has a main body 102 configured to be implanted into the skull bone, a flange 103 configured to serve as a stop to prevent fixture from penetrating through the skull bone, and a tool engaging socket 104 in the form of an internal grip section 105 for easy lifting and handling of fixture 100. The geometrical configuration of the internal grip section may be configured in a manner that allows for engagement with an insertion tool. In accordance with one aspect, the geometric configuration may be in the form of a hex, multi-lobed surfaces, slots or grooves. As shown in FIG. 8 a number of lobe-shaped surfaces 106 is provided in the internal grip section and extends a distance or height (H) 120 in the longitudinal direction of the main body of the fixture parallel to longitudinal axis 107 of the fixture. The lobe-shaped surfaces 106 may be configured to cooperate with an insertion tool having slightly tapered engaging surfaces to engage and lift the fixture.

Figure 9:
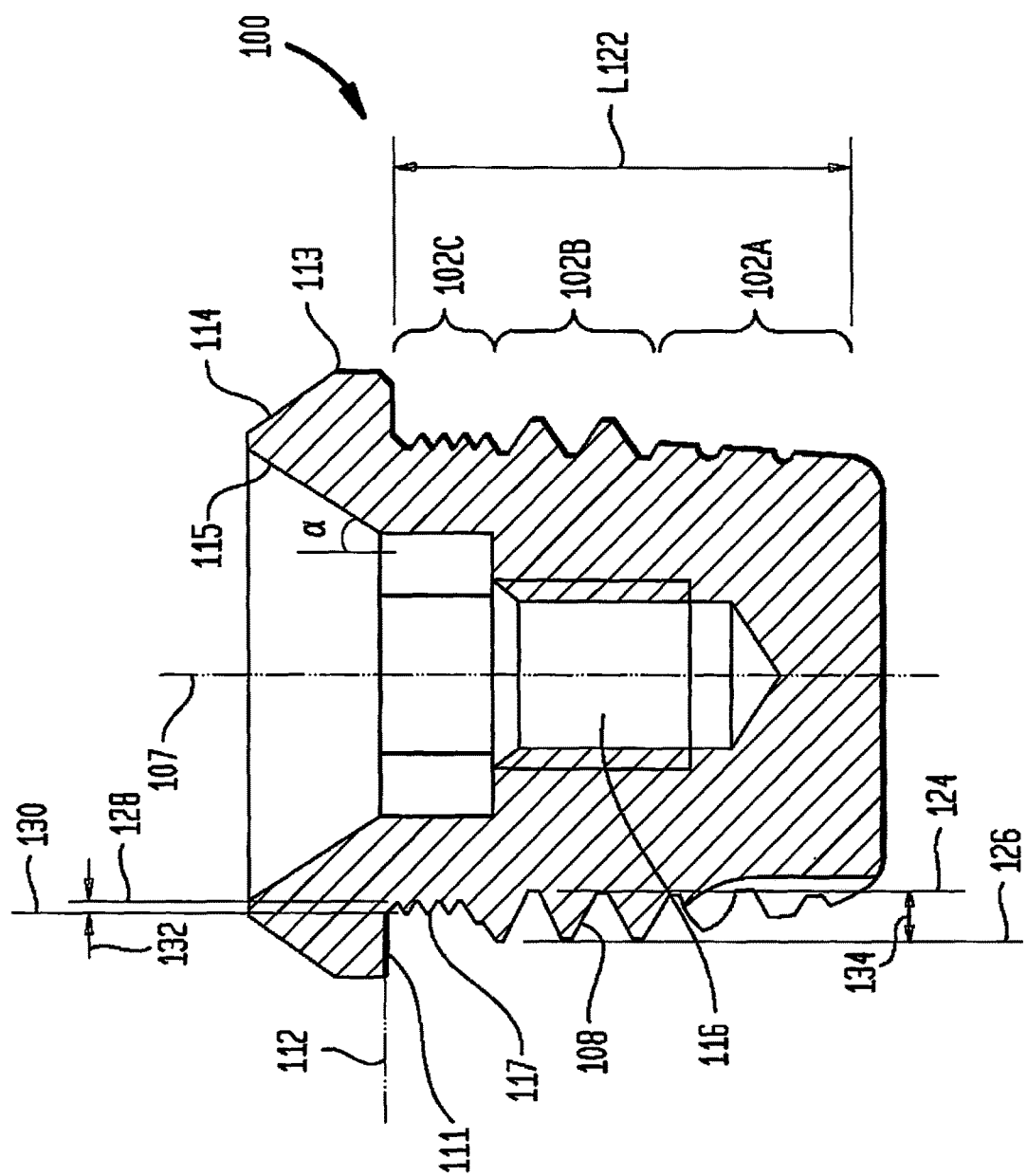
FIG. 9 is a cross-sectional side view of the anchoring element illustrated in FIG. 8.

The main body 102 has a length sufficient to securely anchor fixture 100 into, without penetrating entirely through, the skull bone. The length of main body 102 may therefore depend on the thickness of the skull bone at the implantation site. In one embodiment, main body 102 has a length (L) 122 no greater than approximately 5 mm. Main body 102 further comprises a distal tapered apical portion 102A and a straight, generally cylindrical body comprising two portions, a first portion 102B and a second portion 102C. First portion 102B comprises external threads that form the main screw thread 108 adjacent to the distal tapered apical portion. The second portion 102C is adjacent to the flange. As illustrated in FIG. 9, main screw thread 108 has an inner diameter 124 and an outer diameter 126. In one embodiment, the outer diameter 126 is approximately 3.5-5.0 mm.

As further shown in FIGS. 8 and 9, the distal tapered apical part 102A of main body 102 is configured with self-tapping cutting edges 109. Additional information regarding the self-tapping action is described in greater detail in WO 02/09622, which is hereby incorporated by reference herein. Clearance or relief surfaces 110 may also be provided, wherein the self-tapping cutting edges 109 and the clearance or relief surfaces 110 are provided in an alternating configuration around the main body periphery. This alternating configuration is advantageous because it creates more volume for the cut-off bone chips and therefore reduces the squeezing effect between the fixture 100 and the bone during installation.

As more clearly illustrated in FIG. 9, flange 103 has a planar bottom surface 111 for resting against the outer bone surface, indicated by 112, when the fixture 100 has been screwed into the skull bone. Again, flange 103 prevents the fixture 100 from completely penetrating through the skull bone. Preferably, flange 103 has a diameter which exceeds the peak diameter of the threads by approximately 10-20%. The outer peripheral surface of the flange has a cylindrical part 113 and a tapered top portion 114. The upper end of the flange is designed with an open cavity with a tapered inner side wall 115, a grip section 105, and an inner bottom bore 116 with an internal screw thread for directly or indirectly connecting a hearing aid device or any orbital or ear prosthesis. In order to achieve a stable connection, the inner opening and bore extends to the bottom half of the main body of the fixture 100. The tapered inner side wall 115 forms a seat for a skin-penetrating abutment or the like to create a good connecting fit between the two parts fixture and abutment. The cone angle α may be in the range of about 30-40 degrees. However, the connection with abutment and other parts in the system are not part of this invention and will not be described in any detail here.

In one embodiment, no protruding hex is provided in the embodiment depicted in FIGS. 8 and 9. Rather, the flange forms a smooth, open upper end. The smooth upper end of flange 103 and the absence of any sharp corners provides for improved soft tissue adaptation. Flange 103 also comprises a cylindrical part 113 and a flared top portion 114 which provide sufficient height in the longitudinal direction for internal connection with an abutment sleeve (not shown).

Figure 2:
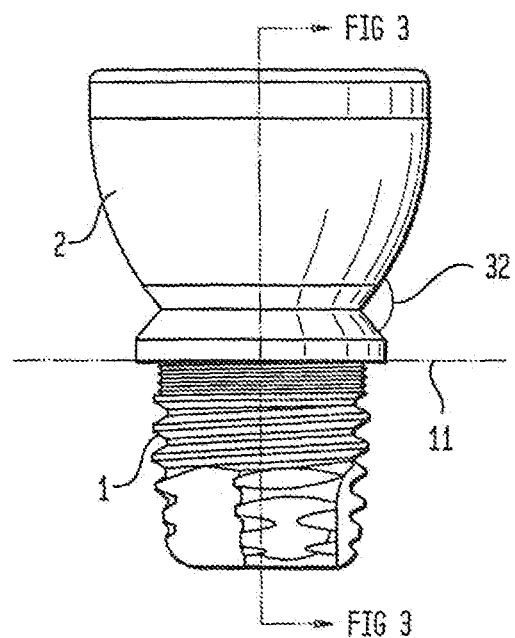
FIG. 2 is a side view of the embodiment of the coupling apparatus illustrated in FIG. 1.

FIG. 2 shows the second portion 102C adjacent to flange 103 having an inner diameter 128 which exceeds the inner diameter 124 of the main threads 108 of the first portion 102B. As noted, this configuration provides a radial compression to the surrounding bone. Preferably the second portion 102C is provided with circumferential grooves 117, having an inner diameter 128 and an outer diameter 130. A drill may then be used having a diameter that is greater than the inner diameter 124 of screw thread 108 of first portion 102B, but less than the outer diameter 130 of second portion 102C of the cylindrical main body of the fixture, that is, 124<Drill Diameter<130. When fixture 100 is inserted into the drilled hole, the second portion 102C compresses the bone to some extent to impart initial stability. The wide diameter portion is located next to the flange so that the compressive action is more concentrated to the hard cortical part of the skull bone tissue.

As mentioned and illustrated in FIGS. 8 and 9, second portion 102C is preferably provided with circumferential grooves 117. In one embodiment, the inner diameter 128 also exceeds the inner diameter 124 of screw thread 108 of first portion 102B. Preferably the height 132 of the groove (130−128=132) is approximately ⅓ or less than the height of screw thread 108 of first portion 102B. In addition to the noted compressive action, such grooves may provide an increased retention between the fixture and the surrounding bone tissue, and spread the forces directed to the abutment more evenly in the bone.

This retention may also be improved by increasing the surface roughness of the bone contacting surfaces of fixture 100. For instance the surface may be modified by means of an abrasive blasting process according to WO 92/05745. In one embodiment the process is used to provide an average surface roughness Sa of about 0.2-2.0 μm, preferably 0.8-1.2 μm, and Sdr(2d/3d)=8-60%, preferably approximately 20-60%.

Circumferentially oriented grooves 117 may extend completely or partly around the periphery of the main body. In the embodiment shown in FIGS. 8 and 9 there are three separate grooves as an example. As an alternative, the grooves may be formed as a screw thread, which may have the same pitch as main screw thread 108, but having a inner diameter 128 that is greater than the inner diameter 124 of main screw thread 108, so that the height of the grooves 117 would be only approximately ⅓ or less of the height 134 of main screw thread 108 (126−124=134). In one embodiment, the extension of the second wide diameter portion 102C in the longitudinal direction of the fixture is about 15-25% of the total height of the fixture.

A method for inserting the fixture may comprise providing the anchoring fixture, drilling a hole, and inserting the anchoring fixture into the hole until the flange contacts the skull bone, wherein the hole has a diameter that is greater than the inner diameter of the first portion and less than the outer diameter of the second portion. No countersinking or removal of cortical bone is used which leaves more good bone left. When fixture 100 is inserted into such a drilled hole, the wider second portion of the fixture, that is, portion 102C next to the flange, provides a certain compression of the cortical bone on the radial direction of the prepared bone hole.

Implants exist in the market that are normally two pieces, one piece consists of the screw-shaped anchoring element (fixture) and the other piece consists of the abutment sleeve for skin penetration. The reason for this two-piece design is the fact that the surgical technique which normally has been used for installing the implants has been carried out as a two-step procedure. In the first step, the fixture is inserted and maintained unloaded during a healing period which may be as long as a few months. After this healing period the second step of the surgical procedure, that is, the connection of the abutment sleeve by means of a screw connection, is carried out. This two-part design facilitates the upgrading of the device if necessary without removing the fixture, and if the abutment sleeve is damaged then it can also be replaced without need of removal of the bone anchored screw.

Although conventional fixtures normally provide sufficiently strong osseointegration, more effective integration between the implant screw and the skull bone is generally desired, particularly for patients having impaired bone quality. Loading of the implant at an earlier stage would also be desired. For persons who cannot benefit from traditional, air conduction hearing aids there are other types of hearing aids on the market commonly referred to as bone anchored hearing aids. Bone anchored hearing aids mechanically transmit sound information to a person's inner ear via the skull bone by means of a vibrator. Such hearing aid devices are typically connected to an anchoring element in the form of a titanium screw implanted in the skull bone behind the external ear so that sound is transmitted via the skull bone to the cochlea (inner ear). This enables the hearing aid to be effective regardless of whether there is a disease or damage in the middle ear. Penetration of the skin makes the vibratory transmission very efficient.

In one aspect of the present invention, an anchoring fixture for permanent anchorage of a prostheses in the skull bone is disclosed, the fixture comprising: a main body configured to be implanted into the bone and having a tapered apical portion and a first substantially cylindrical portion with a screw thread having a first inner diameter, wherein said main body further comprises a second, substantially cylindrical portion adjacent to a bottom surface of the flange having an inner diameter exceeding an inner diameter of said screw thread.

Aspects of the present invention are generally directed to providing a screw-shaped anchoring fixture configured to be anchored in the comparatively thin skull bone and having a certain compressive ability in the radial direction on the thin skull bone in order to improve the initial stability of the fixture.

In one embodiment, the fixture has a main body to be inserted in the skull bone has a first, substantially cylindrical portion provided with a screw thread having a first inner diameter and a second, substantially cylindrical portion next to the planar bottom surface of the flange having a diameter exceeding the inner diameter of the screw thread. Preferably, the second portion has at least one groove extending around the periphery of the cylindrical portion, said groove having a bottom diameter exceeding the inner diameter of the screw thread. Preferably, the groove forms a second screw thread having an inner diameter exceeding the inner diameter of the first, main screw thread. And, the surface of at least the second portion of the main body has been modified in order to increase the surface roughness.

In a preferred method for inserting the fixture a drill is used which has a diameter which is larger than the inner diameter of the screw thread of the first cylindrical portion, but less than the outer diameter of the second cylindrical portion. When the fixture is inserted into such a drilled hole the wider second portion of the fixture, i.e. the portion next to the flange, provides a certain compression of the bone, specifically the cortical bone, in the radial direction of the bone hole.

Also as can be seen in FIG. 9, flange 103 has a planar bottom surface for resting against the outer bone surface, indicated by 112 in FIG. 9, when the screw has been screwed down into the skull bone. The flange has a diameter which exceeds the peak diameter of the thread width by 10-20%. The outer peripheral surface of the flange has a cylindrical part in a tapered top portion.

It should be understood that compared to traditional flange fixtures there is no protruding hex in an embodiment, the flange itself is instead forming a smooth, open upper surface. The flange itself is also designed with a cylindrical part which makes the flange thicker than previously, substantially to make it the same height as the previous flange plus the hex. Thereby there is enough space in the longitudinal direction for the internal connection. Also the smooth upper surface, without a protruding hex, provides an improved soft tissue adaptation without any sharp corners.

According to the invention said second portion next to the flange has a diameter which exceeds the inner diameter of the threads of the first portion of the main body. The reason for this feature is the possibility to provide a certain compression of the surrounding bone in the radial direction of the prepared bone hole, by this portion. Preferably the second portion is provided with circumferential grooves, having an inner diameter and an outer diameter.

The retention noted above can also be improved by increasing the surface roughness of the bone contacting surfaces of fixture 1, specifically the surface of the second portion, with or without grooves, but preferably all the surfaces "under the flange", including the planar bottom surface 111 of the flange. For instance the surface can be modified by means of an abrasive blasting process according to WO 92/05745. In one embodiment the process is used to provide an average surface roughness Sa of 0.2-2.0 µm, preferably 0.8-1.2 µm, and Sdr(2d/3d)=8-60%, preferably 20-60%.

A method for inserting the fixture comprises the use of a drill which has a diameter C which is larger than the inner diameter 126 of the screw thread of the first cylindrical portion, but less than the outer diameter 130 of the second cylindrical portion. No countersinking or removal of cortical bone is used which leaves more good bone left. When fixture 100 is inserted into such a drilled hole, the wider second portion of the fixture, i.e., the portion next to the flange, provides a certain compression of the cortical bone on the radial direction of the prepared bone hole.

In an exemplary embodiment, there is an anchoring fixture for permanent anchorage of a prostheses m the skull bone, comprising: a main body configured to be implanted into the bone and having a tapered apical portion and a first substantially cylindrical portion with a screw thread having a first inner diameter, wherein said main body further comprises a second, substantially cylindrical portion adjacent to a bottom surface of the flange having an inner diameter exceeding an inner diameter of said screw thread.

In an exemplary embodiment, there is a fixture as described above, wherein the main body further comprises: a flange having a substantially planar bottom surface which provides a stop for the anchoring element when it is screwed down into the comparatively thin skull bone.

In an exemplary embodiment, there is a fixture as described above, wherein the second portion has one or more grooves circumferentially extending around the periphery of the cylindrical portion.

In an exemplary embodiment, there is a fixture as described above, wherein the circumferentially-oriented grooves extend completely around the periphery of the main body.

In an exemplary embodiment, there is a fixture as described above, wherein circumferentially oriented grooves are extending partly around the periphery of the main body.

In an exemplary embodiment, there is a fixture as described above, wherein the height of the groove is less than the height of the screw thread of the first portion. In an exemplary embodiment, there is a fixture as described above, wherein the grooves are formed as a screw thread, preferably having the same pitch as the main screw thread, but with a wider inner diameter. In an exemplary embodiment, there is a fixture as described above, wherein at least the surface of said second portion has been modified in order to increase the surface roughness.

In an exemplary embodiment, there is a fixture as described above, wherein the surface has been modified by means of an abrasive, blasting process. In an exemplary embodiment, there is a fixture as described above, wherein the screw thread surface and the bottom surface of the flange have been modified by means of an abrasive, blasting process.

In an exemplary embodiment, there is a fixture as described above, wherein the extension of the second wide diameter portion in the longitudinal direction of the fixture would be around 15-25% of the total height of the fixture. In an exemplary embodiment, there is a fixture as described above, wherein the tool engaging socket comprises an internal grip section for easy lifting and handling of the fixture, said grip section having a geometrical configuration in the form of a hex, multi-lobed surfaces, slots, grooves or the like. In an exemplary embodiment, there is a fixture as described above, wherein the internal grip section comprises a number of lobe-shaped surfaces extending in the longitudinal direction of the main body of the fixture parallel to the longitudinal axis of the fixture, which lobe-shaped surfaces are intended to cooperate with an insertion tool. In an exemplary embodiment, there is a fixture as described above, wherein the upper end surface of the flange is designed with an open cavity with a tapered inner side wall, connected with said grip section which in turn goes into an inner bottom bore with an internal screw thread allowing a hearing aid device or any orbital or ear prosthesis to be connected to the anchoring element.

In an exemplary embodiment, there is a fixture as described above, wherein the open cavity with a tapered inner side wall is forming a seat for a skin-penetrating abutment or the like to create a good connecting fit between the anchoring element and the abutment. In an exemplary embodiment, there is a fixture as described above, wherein the tapered inner side wall has a cone angle in the range of approximately 30-40 degrees. In an exemplary embodiment, there is a fixture as described above, wherein the prosthesis is a hearing aid device.

In an exemplary embodiment, there is a fixture as described above, wherein the flange further comprises a tool engaging socket.

In an exemplary embodiment, there is a method for inserting an anchoring element according to that detailed above into the skull bone, comprising the use of a drill having a diameter which exceeds the inner diameter of the screw thread of said first portion but less than the outer diameter of the second portion of the main body.

Aspects of the present invention are generally directed to a bone anchored coupling apparatus in which the percutaneous surfaces of an implanted fixture component and an associated abutment component are configured so as to reduce the risk for micro gaps and unwanted micro-leakage, preferably regardless of any imperfectness of the mating surfaces and any incorrect tightening torques.

In certain embodiments, the coupling apparatus has a smooth outer contour fazing the surrounding soft tissue to avoid unwanted pockets, gaps or sharp corners in the tissue-device interface. In particular embodiments, the regions of the fixture and the abutment components which mate with each other have inverse conically-shaped regions such that, when mated, the Fixture forms the bottom of the hourglass shape while the abutment forms the top of the hourglass shape. Preferably, the dimensions of the hourglass configuration are such that the patient's skin abuts the narrow region of the hourglass configuration.

In one embodiment, the upper end surface of the fixture has an open cavity with a tapered interior surface thrilling a seat for the abutment formed with a tapered exterior side wall to create a good connecting fit between the fixture and abutment.

A well known problem with percutaneous implants is infection and inflammation at the skin-implant interface resulting from bacterial colonization in the area around the interface. The coupling apparatus of the present invention in the integration of the skin to the coupling apparatus thereby decreasing the likelihood that a gap will form between the two. Such gaps are, unfortunately, an ideal environment liar the bacteria. By creating an integration of the skin to the coupling apparatus the adverse skin reactions associated with bone anchored percutaneous implants may be reduced.

Creating integration between the skin and the implant requires that the implant is suitable for this purpose and that the soft tissue does not dissociate itself from the skin-penetrating implant abutment by encapsulating the abutment in fibrous tissue. In US Provisional Patent Application Ser. No. 60/951,163 filed Jul. 20, 2007, entitled "Bone Anchor Fixture For Medical Prosthesis," it is suggested a surface modification which is supposed to reduce such adverse skin reactions. However, it is also desirable that the entire implant device is designed in such a way that gaps or pockets which could give rise to infections are eliminated or at least minimized.

Embodiments of the present invention may be used in connection with hearing aid devices of the bone conduction type, that is, hearing aid devices by which the sound is transmitted via the skull bone directly to the inner ear of a person with impaired hearing. However, embodiments of the present invention may also be configure for use in connection with other types of hearing aid devices for anchorage in the skull bone and for ear or orbital prostheses which are also anchored in the skull bone. Other applications of the present invention are also contemplated.

Figure 1:
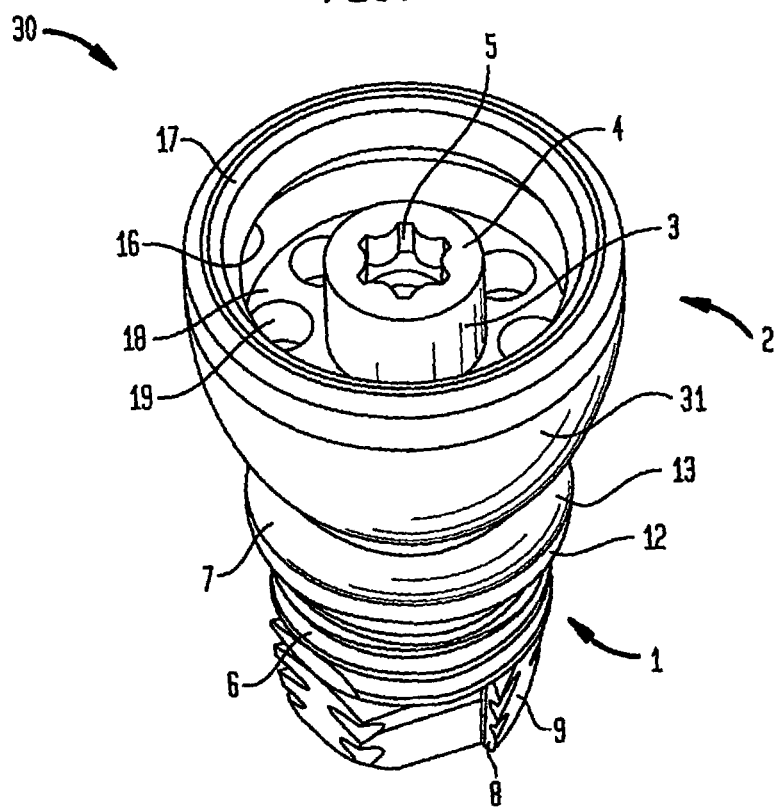
FIG. 1 is a perspective view of the coupling apparatus m accordance with one embodiment of the present invention.

FIG. 1 is a perspective view of a bone anchored coupling apparatus according to one embodiment of the present invention. Coupling apparatus 30 is illustrated in FIG. 1 with a screw-shaped bone anchor fixture 1 and a skin-penetrating abutment 2. The two parts are connected by an elongate coupling shall 3 having, in one embodiment, a cylindrical screw head 4 protruding in FIG. 1. Screw head 4 has an internal hex or hex tubular configuration 5 for a cooperating insertion tool, which is not part of the invention and therefore not illustrated here.

In one embodiment, fixture 1 is made of titanium which has a known ability to integrate into surrounding bone tissue, a phenomenon commonly referred to as osseointegration. Fixture 1 has a main body with an outer screw thread 6 which is intended to be installed into the skull bone. Fixture 1 also comprises a flange 7 configured to inaction as a stop when fixture 1 is installed into the skull bone. In this embodiment, fixture 1 further comprises a tool-engaging socket 40 having an internal grip section 40A for easy lifting and handling of fixture 1. Tool-engaging socket 40 and the internal grip section are described in U.S. Provisional Patent Application Ser. No. 60/951,163 filed Jul. 20, 2007, entitled "Bone Anchor Fixture For A Medical Prosthesis, " which is hereby incorporated by reference herein.

The main body of fixture 1 is shorter than 5 mm to avoid penetrating through the thin skull bone. The main body has a tapered apical proximate end 1A and a straight, generally cylindrical body. The outer diameter of screw thread 6 of fixture 1 is about 3.5 to 5.0 mm.

In the illustrative embodiment, a distal region 1B of fixture 1 is fitted with, three self-tapping cutting edges 8 formed into the exterior surface of the fixture. Further details of the self-tapping features are described in International Patent Application WO 02/09622, which is hereby incorporated by reference herein.

That part of the screw body which follows behind the self-tapping cutting edges 8 when the screw is installed in the bone can be provided with a clearance or relief surface 9. Such design has two effects. First, any squeezing effect between the screw and the bone during installation of the screw is reduced. And second, more volume for the cut-off bone chips is created.

Figure 3:
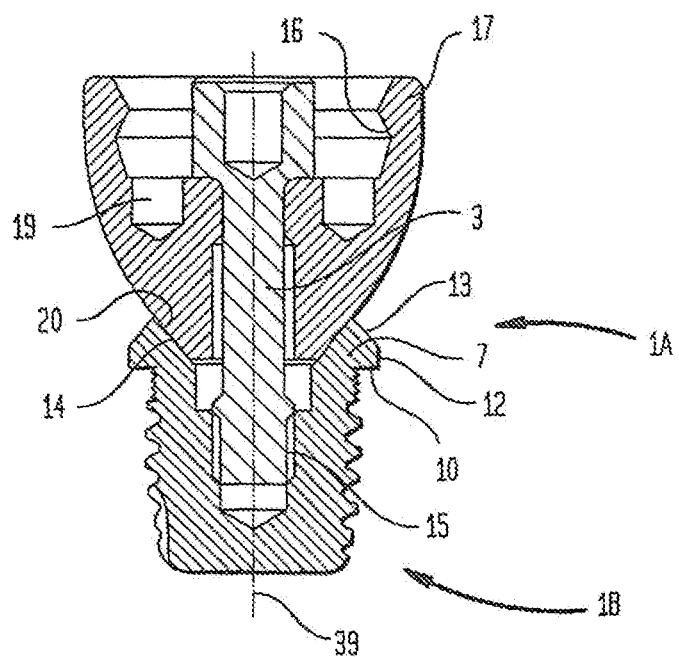
FIG. 3 is a cross-sectional side view of the embodiment of the coupling apparatus illustrated in FIG. 1.

As more clearly illustrated in FIGS. 2 and 3, flange 7 has a planar bottom surface 10 for resting against the outer bone surface, indicated by 11 in the figures, when anchoring fixture 1 has been screwed down into the skull bone. Flange 7 has a diameter which exceeds the peak diameter of the threads by approximately 10-20%. It should be appreciated that although flange 7 is shown as being circumferential, it has a different configuration in alternative embodiments. Also, the size of flange 7 may vary depending on the particular application.

The outer peripheral surface 36 of flange 7 has a cylindrical part 12 and a tapered top portion 13. Upper end surface 7A of flange 7 is designed with an open cavity 14A with a tapered interior surface 14, connected with the grip section 40A which in turn goes into an inner bottom bore. IS with an internal screw thread for connecting abutment screw 3.

Figure 4:
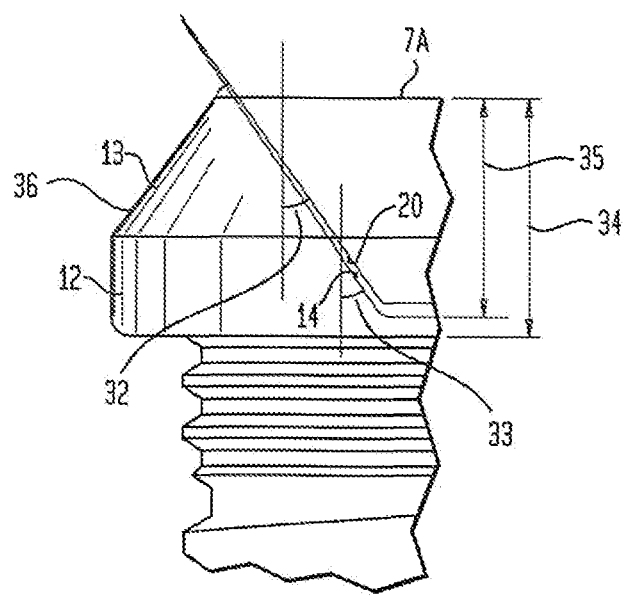
FIG. 4 is a partial view of a proximate end of the fixture illustrating the tapered connection between the fixture and the abutment components of the coupling apparatus illustrated in FIG. 1, in accordance with one embodiment of the present invention.

To increase the stability of the coupling between fixture 1 and abutment 2, open cavity 14A extends from flange 7 to, preferably, distal region 1B of fixture 1. Tapered inner side wall 14 forms a seat for abutment 2 to create a good connecting fit between the two parts fixture and abutment. As shown in FIG. 4, cone angle 32 of tapered interior contour 14 of fixture 1 might be in the range of approximately 30-40 degrees.

It should be understood that compared to traditional flange fixtures there is no protruding hex in this case, the flange itself is instead forming a smooth, open upper surface 7a. Flange 7 also comprises a cylindrical part 12 which, together with the tapered upper part 13, makes flange 7 thicker than previously, thereby there is enough space in the longitudinal direction of the fixture for the internal connection, and the tapered seat 14 is entirely within the height 34 of flange 7, as illustrated in FIG. 4. Also the smooth upper surface 7a, without a protruding hex, provides an improved soft tissue adaptation without any sharp corners.

The skin penetrating part of the implant comprises a substantially conical abutment component 2. Abutment 2 has an inner annular flange 16 at its upper edge 17 in order to cooperate with other components (not shown) by means of snap-in action or the like. Abutment 2 has an internal shoulder 1 with a central, opening for connecting shaft 3 and a number of peripherally arranged through holes or recesses 19 used for a tool such as that illustrated in WO 2004/105650, which is hereby incorporated by reference herein.

It should be appreciated that the three main components: fixture 1, abutment 2 and coupling screw 3, may be delivered separately or they can be delivered in the form of a pre-mounted device as illustrated in WO 2004/105650. This means that the implant device is delivered to the surgeon pre-mounted in its package to facilitate installing the entire device in one step. Abutment 2 may be pre-mounted to the fixture at the manufacturing site with the correct tightening torque alleviating the need for the surgeon to be aware of the correct tightening torque, as well as the need to handle the separate pieces.

In contrast to traditional implants with outer fixture hex for tool engagement, the recesses 19 in the abutment sleeve are used when installing the implant. These recesses are located on the upper part of the implant device and more visible than a traditional outer hex.

According to one embodiment of the present invention, abutment 2 has a substantially curved, conical outer surface with the upper edge 17 having the wider diameter and the bottom, fixture-connecting part having a smaller diameter. The bottom part of the outer surface has a contour 20 adapted to the tapered inner contour 14 of the fixture to create a good connecting fit between the two parts fixture and abutment. Such a fit between conical shaped surfaces provides an axially well-defined fit when the two parts are assembled, but also a fit which loosens easily when the two parts are disassembled.

As noted, in certain embodiments, it is desirable to provide an implant device in which the risk for micro-leakage is reduced. Designing the upper part of the fixture and the lower part of the abutment with a conical fit reduces the risk for micro-gaps and unwanted micro-leakage irrespective of any imperfectness of the contact surfaces and any incorrect tightening torques.

The cone angle 33 of tapered portion 20 of abutment 2 is in the range of 30-40 degrees, similar to cone angle 32 of tapered fixture seat 14. Preferably, there is a small difference between cone angles 32, 33, perhaps in the range of approximately 1-5 degrees and, preferably, approximately 1 degree.

In certain embodiments, the skin-contacting surface of abutment 2 is modified in such a way that the shear modulus of the skin-contacting part of abutment 2 is reduced to less than 35 GPa. For example, in one embodiment, the surface of the skin-contacting part of the percutaneous implant abutment 2 is coated with a biocompatible polymer or a ceramic material. In one embodiment, the coating has a thickness of approximately 0.001-50.0 μm. As an alternative, or in combination, a surface increasing treatment can be provided to the surface resulting in a roughness value $S_a$ Of 0.5-10 μm. Such surface embodiments reduce the shear modulus and, hence, also reduce specific adverse skin reactions. Surface modifications of this type are discussed in more detail in the co-pending patent application incorporated by reference elsewhere herein.

As illustrated in FIG. 4, an hourglass waist angle 38 defined to be between exterior peripheral surface 36 of tapered portion 13 of flange 7 and the tapered lower portion 20 of abutment 2 is greater than 90 degrees, in order to achieve a smooth outer contour facing the soft tissue. It is anticipated that such a design will substantially and optimally eliminate unwanted pockets where bacteria might grow. This is in contrast to many traditional implant devices of this type in which a comparatively sharp interface has been formed between the upper side of a flat flange and the outer contour of the abutment.

As noted, encouraging integration between the skin and the coupling apparatus is facilitated by a stable connection, that is, a tight fit, between the abutment and fixture components. This is also facilitated by a smooth outer contour of the coupling apparatus, as well as the coupling apparatus having a suitable surface structure.

However, the implant device should also be designed in such a way that it is easy to handle together with instruments and components used for installation and control of the implant device. As noted, the surgical technique normally used for installing the implants has been carried out as a two-step procedure. In the first step the implant is inserted and maintained unloaded during a healing period of some months or so. During this healing period it is important as well that there is no micro-leakage and bacteria colonization. The upper part of the abutment sleeve is normally covered by the soft tissue, the skin, during the healing period. As the upper part of abutment 2 is open a healing cap device may then be used for covering the opening in the abutment.

According to another aspect of the present invention, a healing cap 37 is, in certain embodiments, a two-part device comprising a snap-in connecting platform 21 and a cap 22, with the two parts connected by means of a flexible band 23. This design makes it easy and safe for the surgeon to handle.

Figure 6A:
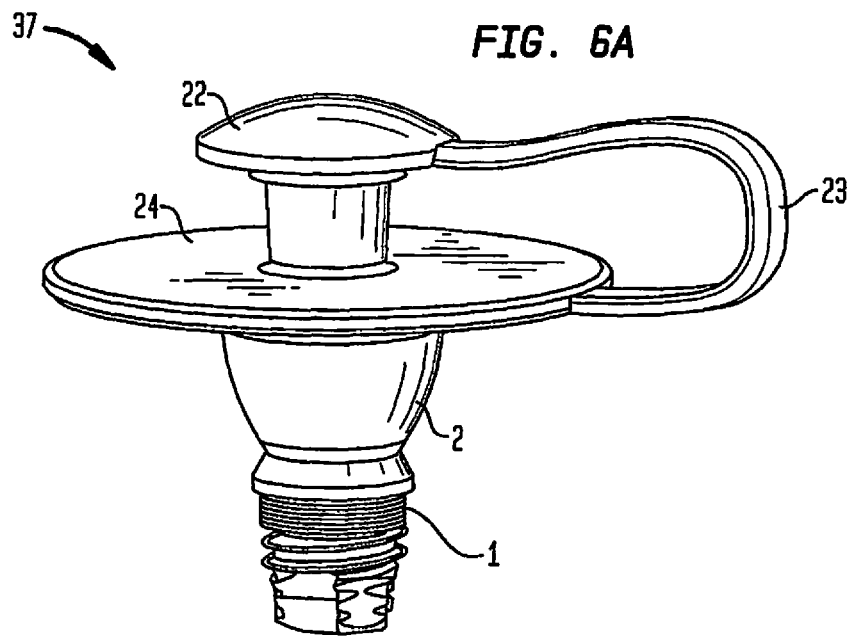
FIG. 6A is a side view of a healing cap with the coupling apparatus illustrated in FIG. 1, with the healing cap in a closed orientation, in accordance with one embodiment of the present invention.
Figure 6B:
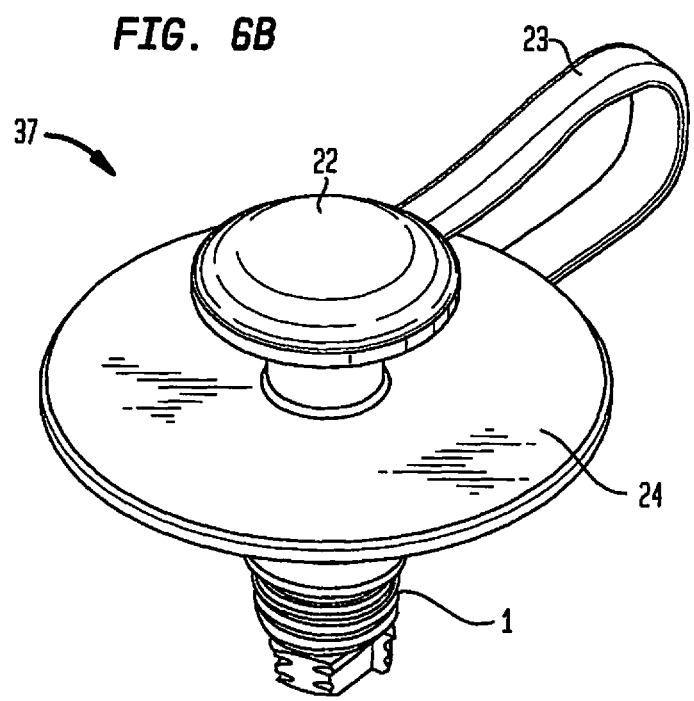
FIG. 6B is a perspective view of the healing cap illustrated in FIG. 6A.
Figure 7A:
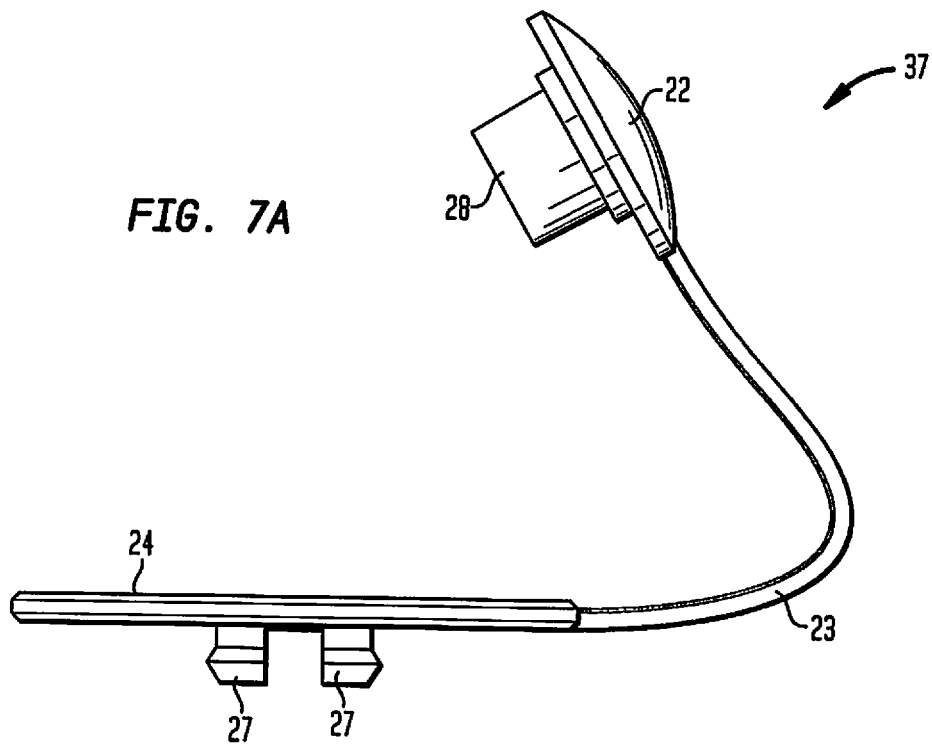
FIG. 7A is a side view of the healing cap illustrated in FIGS. 6A and 6B, with the healing cap in an open orientation.
Figure 7B:
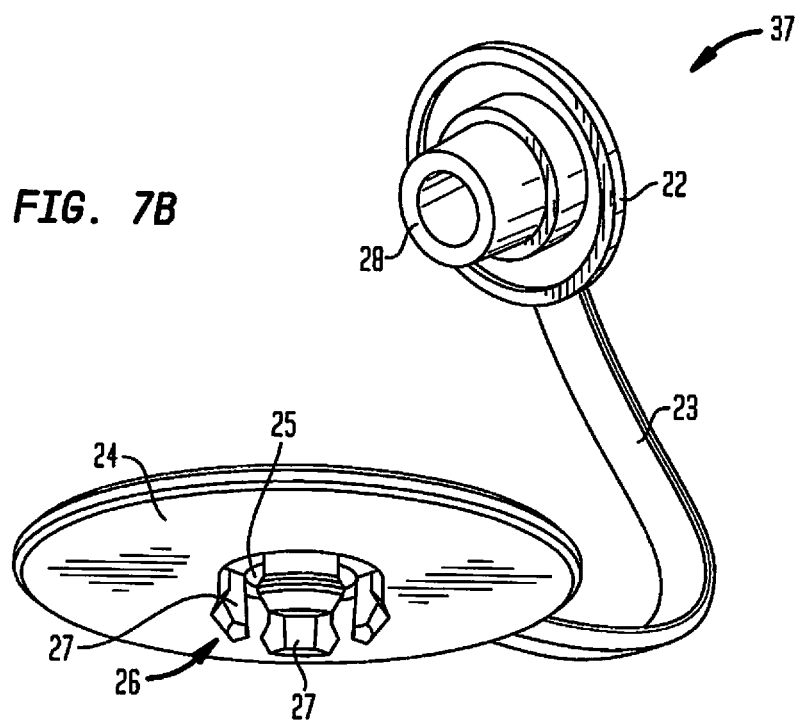
FIG. 7B is a perspective view of the healing cap illustrated in FIG. 7A.

Specifically, snap-in connecting part 21 comprises a flat disc-shaped member 24 provided with a central through opening 25 and a lower, central protruding portion 26 with a number of protruding, flexible members 27 arranged to cooperate with said inner annular flange 16 on the abutment sleeve in connected position. Cap 22 comprises a lower, cylindrical sleeve-shaped portion 28 arranged to be inserted into the annular spacing formed between the flexible members 27 and the protruding screw head 4 of the abutment screw 3. Cap 22 provides a closure for the through hole in the abutment sleeve as well as a locking member for snap-in connecting part 21. Healing cap 37 is preferably made of a plastic material. In FIGS. 6A and 6B, sleeve-shaped portion 28 is illustrated with a cylindrical shape. However, it should be understood that the sleeve could have any other shape, such as a squared or rectangular shape, depending on the connecting parts.

Figure 5:
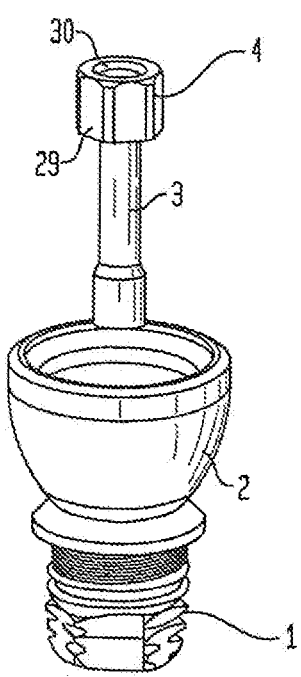
FIG. 5 is a perspective view of an elongate coupling shaft having, in this embodiment, a screw head with an external hex and bore with an internal screw thread.

In FIG. 1, connecting or coupling shaft 3 is shown to have a screw head 4 with an internal hex or tubular hex configuration 5 for a cooperating insertion tool or the like. In FIG. 5 coupling shaft 3 is illustrated as having a screw head 4 with an external hex geometry 29 and a bore with an internal screw thread 30. The external hex geometry 29 is then used for the screw tightening and the internal screw thread 30 used for connecting measuring probes or the like for controlling purposes. Specifically, the screw head could be used for connecting a Resonance Frequency Analyzer (RFA) probe for measuring implant stability and osseointegration. In one embodiment, an M 1.6 screw is used. In combination with the conical fit the M 1.6 screw gives in the given design enough torque to secure the assembly and yet better elastic deformation of the screw which gives an assembly that has less risk to un-screw itself.

The invention is not limited to the embodiments illustrated in the drawings but can be varied within the scope of the accompanying claims. Specifically it should be understood that the entire implant device—including fixture, abutment, abutment screw and healing cap—could be installed at the same session, with a subsequent healing period, instead of the traditional procedure with a separate installation and healing period for the fixture only.

Further features and advantages of the present invention may be found in U.S. Provisional Application No. 60/951,169, entitled "Coupling Apparatus For a Bone Anchored Hearing Device," and filed Jul. 20, 2007, and U.S. Provisional Application No. 60/951,163, entitled "Bone Anchor Fixture for a Medical Prosthesis," and filed Jul. 20, 2007, which are hereby incorporated by reference herein.

In an exemplary embodiment, there is a coupling apparatus for anchorage of a prosthesis to a patient's skull bone, comprising: an elongate anchoring fixture comprising an external screw thread for penetrating the bone, and a flange that abuts the bone when the fixture is implanted, wherein a proximate end of the fixture has an open cavity with a tapered interior contour; and a skin-penetrating abutment, detachably connectable to said fixture, comprising a substantially conical exterior surface with a wider proximate region and a narrower distal region having a tapered exterior contour that fits within said tapered interior contour of said open cavity. In an exemplary embodiment, the prosthesis is a hearing prosthesis.

In an exemplary embodiment, there is a coupling apparatus for a bone anchored hearing device for permanent anchorage of hearing aid devices or extra-oral prostheses in the form of ear and orbital prostheses in the skull bone. The implant device comprises a screw-shaped anchoring fixture to be inserted into the skull bone and a skin-penetrating abutment configured to be connected to the fixture by means of a screw connection. The fixture comprises a main body with an external screw thread and a flange having a substantially planar bottom surface which provides a stop for the anchoring element when it is screwed down into the comparatively thin skull bone. The skin-penetrating abutment comprises a substantially conical outer surface having an upper edge with a wider diameter and a bottom, fixture-connection part having a smaller diameter. The upper end surface of the fixture is designed with an open cavity with a tapered inner contour forming a seat for the bottom part of the abutment which is also formed with an outer, tapered contour to create a good connecting fit between the two components fixture and abutment by means of conically shaped contact surfaces.

An embodiment includes a screw-shaped anchoring fixture for permanent anchorage of hearing aid devices or other extra-oral prostheses in the skull bone. The anchoring element comprises a main body which is intended to be inserted into the skull bone. The main body has a tapered apical portion and a first substantially cylindrical portion with a screw thread having a first inner diameter, a flange having a substantially planar bottom surface which provides a stop for the anchoring element when it is screwed down into the comparatively thin skull bone and an internal tool engaging socket. The main body further comprises a second substantially cylindrical portion next to the planar bottom surface of the flange having a diameter exceeding the inner diameter of said screw thread. The method for inserting the fixture includes the use of a drill which has a diameter which is larger than the inner diameter of the screw thread of the first cylindrical portion but less than the outer diameter of the second cylindrical portion. When the fixture is inserted into such a drilled hole the wider second portion of the fixture, that is, the portion next to the flange, provides a certain compression of the cortical bone in the radial direction of the prepared bone hole which should be beneficial for the initial stability of the fixture in the skull bone.

In an embodiment, there is an anchoring fixture for anchoring a prosthesis to a skull bone comprising: a main body configured to be implanted into the bone, the main body comprising a distal tapered apical portion and a first portion adjacent to the distal tapered apical portion and a second portion adjacent to the first portion; wherein the first portion has a first inner diameter and the second portion has a second inner diameter; and wherein the second inner diameter is greater than the first inner diameter.

In an exemplary embodiment, there is the fixture described above, further comprising: a flange configured to function as a stop when main body is implanted in the skull bone. In an exemplary embodiment, there is the fixture described above, wherein the fixture comprises a material capable of integrating into the surrounding bone tissue. In an exemplary embodiment, there is the fixture described above, wherein the material is titanium. In an exemplary embodiment, there is the fixture described above, further comprising: a tool engaging socket for lifting and handling the fixture by a cooperating insertion tool. In an exemplary embodiment, there is the fixture described above, wherein the tool engaging socket comprises an internal grip section. In an exemplary embodiment, there is the fixture described above, wherein the internal grip section has a geometric configuration, wherein said geometric configuration is any one or a combination of: a hex, a multi-lobed surface, slots, and grooves. In an exemplary embodiment, there is the fixture described above, wherein the internal grip section has a multi-lobed surface and grooves.

In an exemplary embodiment, there is the fixture described above, wherein the main body has a length that is less than the bone thickness at the site of implantation.

In an exemplary embodiment, there is the fixture described above, wherein the main body has a length that is less than approximately 5 mm. In an exemplary embodiment, there is the fixture described above, wherein the distal tapered apical portion comprises alternating self-tapping cutting edges and clearance or relief surfaces along a periphery of the distal tapered apical portion. In an exemplary embodiment, there is the fixture described above, wherein the first and second portion of the main body is generally cylindrical. In an exemplary embodiment, there is the fixture described above, wherein the first portion further comprises main screw threads, wherein said main screw threads have an inner diameter, an outer diameter, and a height. In an exemplary embodiment, there is the fixture described above, wherein the second portion further comprises circumferential grooves, the circumferential grooves having an inner diameter, an outer diameter, and a height. In an exemplary embodiment, there is the fixture described above, wherein the circumferential grooves extend completely around the main body. In an exemplary embodiment, there is the fixture described above, wherein the circumferential grooves extend partially around the main body. In an exemplary embodiment, there is the fixture described above, wherein the inner diameter of the circumferential grooves is less than the outer diameter of the main screw threads.

In an exemplary embodiment, there is the fixture described above, wherein the inner diameter of the circumferential grooves is greater than the outer diameter of the main screw threads. In an exemplary embodiment, there is the fixture described above, wherein the height of the main screw threads is greater than the height of the circumferential grooves. In an exemplary embodiment, there is the fixture described above, wherein circumferential grooves are formed as a screw thread having a groove pitch that is the same as the main screw thread pitch. In an exemplary embodiment, there is the fixture described above, wherein the height of the circumferential grooves is approximately 33% of the height of the main screw threads. In an exemplary embodiment, there is the fixture described above, wherein the height of the circumferential grooves is less than approximately 33% of the height of the main screw threads.

In an exemplary embodiment, there is the fixture described above, wherein the flange further comprises an upper end and an open cavity disposed at the upper end, the open cavity further comprising a tapered inner side wall adjacent to the internal grip section.

In an exemplary embodiment, there is the fixture described above, further comprising: an inner bottom bore adjacent to the internal grip section, the inner bottom bore comprising internal screw threads. In an exemplary embodiment, there is the fixture described above, wherein the prosthesis is a hearing aid device. In an exemplary embodiment, there is the fixture described above, wherein the main body has a surface roughness sufficient to retain of the fixture in the bone. In an exemplary embodiment, there is the fixture described above, wherein the surface roughness has a value of about 0.2 µm to about 2.0 µm. In an exemplary embodiment, there is the fixture described above, wherein the surface roughness has a value of about 0.8 µm to about 1.2 µm.

In an exemplary embodiment, there is an anchoring fixture for anchoring a prosthesis to a skull bone comprising: a main body configured to be implanted into the skull bone, the main body comprising a distal tapered apical portion, a first threaded portion having a first diameter adjacent to the distal apical portion, and an adjacent second threaded portion having a second diameter; and a flange adjacent to the second threaded portion, the flange comprising a planar bottom surface adapted to rest on top of the skull bone when the main body is implanted into the skull bone; wherein the second diameter is greater than the first diameter.

In an exemplary embodiment, there is a method for installing the anchoring fixture into a skull bone, the method comprising: providing an anchoring fixture, drilling a hole having a diameter into the skull bone, wherein the inner diameter of the main screw threads is less than the diameter of the hole, and further wherein the diameter of the hole is less than the outer diameter of the circumferential grooves; and inserting the anchoring fixture into the hole until the flange contacts the skull bone. In an exemplary embodiment, the inserting step comprises screwing the anchoring fixture into the skull bone.

The invention is not limited to the embodiment illustrated in the drawings but may be varied within the scope of the accompanying claims. Specifically, it is understood that other types of abrasive methods, coatings etc, may be used for increasing the roughness of bone-contacting surfaces. Such methods are known per se and not described here in any detail.

What is claimed is:

1. An anchoring fixture for anchoring a prosthesis to a skull bone, comprising:
  a main body configured to be implanted into the skull bone, the main body comprising a tapered portion, the main body also comprising a screw thread apparatus including a screw thread; and
  a projection extending outward away from a longitudinal axis of the anchoring fixture beyond a maximum lateral extension of the screw thread, wherein
  a first portion of the main body has a first inner diameter and a second portion of the main body has a second inner diameter,
  the second portion is located closer to the projection than the first portion,
  the second inner diameter is greater than the first inner diameter, and
  the anchoring fixture is configured for anchoring a hearing prosthesis component to the skull bone at a location behind an external ear so that sound is transmitted from the hearing prosthesis via the skull bone to a cochlea.

2. An anchoring fixture comprising:
  a main body having a screw thread having a varying outer diameter; and
  a means for preventing penetration of the anchoring fixture through a skull bone of a recipient, wherein
  the anchoring fixture is configured to anchor a hearing prosthesis to the skull bone at a location behind an external ear of the recipient so that vibrations based on sound are transmitted from the hearing prosthesis via the skull bone to a cochlea in the recipient of the anchoring fixture, and
  a maximum diameter of the screw thread is greater than a length from a bottom of the means for preventing penetration to a distal end of the anchoring fixture.

3. The anchoring fixture of claim 1, wherein:
  at least a portion of the screw thread apparatus has a logarithmic conical shape when the anchoring fixture is viewed from the side.

4. The anchoring fixture of claim 2, wherein:
  the anchoring fixture is threaded all the way up to the means for preventing penetration.

5. The anchoring fixture of claim 2, wherein:
the anchoring fixture is equipped with a groove under the means for preventing penetration.

6. The anchoring fixture of claim 2, wherein:
the anchoring fixture is equipped with a groove under the means for preventing penetration; and
the screw thread goes all the way up to the means for preventing penetration.

7. The anchoring fixture of claim 2, wherein the means for preventing penetration has a maximum diameter that exceeds a peak diameter of the screw thread by approximately 10-20%, wherein the screw thread goes all the way up to the means for preventing penetration and the anchoring fixture is configured to exert a compression force onto skull bone in a radial direction, thereby stabilizing the anchoring fixture in the skull bone when implanted therein.

8. The anchoring fixture of claim 2, wherein the anchoring fixture has a groove that is in contact with the screw thread.

9. The anchoring fixture of claim 2, wherein the anchoring fixture does not have a circumferential groove that extends around a periphery of a cylindrical portion of the anchoring fixture.

10. The anchoring fixture of claim 1, further comprising:
a circumferential groove, wherein the circumferential groove is coincident with a portion of the screw thread.

11. The anchoring fixture of claim 1, wherein the anchoring fixture comprises a wide portion that is located, with respect to a side of the projection, on a threaded side of the anchoring fixture, wherein the wide portion is configured to exert a compression onto the skull bone in a radial direction, to stabilize the anchoring fixture in the skull bone when the anchoring fixture is implanted, and wherein the anchoring fixture comprises a circumferential groove that extends around the wide portion of the anchoring fixture.

12. The anchoring fixture of claim 1, wherein:
the main body includes a threaded section including the screw thread;
the projection includes an outermost surface; and
a cross section lying on and parallel to the longitudinal axis includes a portion, relative to direction along the longitudinal axis, between the threaded section and the outermost surface, that includes at least five separate surfaces that have respective directions of extension relative to the longitudinal axis are respectively different from each other.

13. The anchoring fixture of claim 1, wherein:
the main body includes a threaded section including the screw thread;
the projection includes an outermost surface; and
a cross section lying on and parallel to the longitudinal axis includes a portion, relative to direction along the longitudinal axis, between the threaded section and a flat surface of the projection that is perpendicular to the longitudinal axis and faces the skull bone when the anchoring fixture is implanted in the skull bone, that includes at least two separate surfaces that have respective directions of extension relative to the longitudinal axis that are respectively different from each other.

14. The anchoring fixture of claim 1, wherein:
the main body includes a threaded section including the screw thread;
the projection includes an outermost surface; and
a cross section lying on and parallel to the longitudinal axis includes a portion, relative to direction along the longitudinal axis, between the threaded section and a flat surface of the projection that is perpendicular to the longitudinal axis and faces the skull bone when the anchoring fixture is implanted in the skull bone, that includes at least three separate surfaces that have respective directions of extension relative to the longitudinal axis that are respectively different from each other.

15. An anchoring fixture for anchoring a hearing prosthesis to a cranial section of a skull bone, comprising:
a threaded body including a screw thread configured to be implanted into the skull bone, the threaded body comprising a first portion and a second portion adjacent the first portion; and
a non-threaded body establishing a maximum outer diameter of the anchoring fixture in a direction normal to a longitudinal axis of the anchor fixture, which maximum diameter exceeds a peak diameter of the screw thread by approximately 10-20%, wherein
the first portion has a first maximum outer diameter and the second portion has a second maximum outer diameter,
the second portion is distal the first portion; and
the first maximum outer diameter is greater than the second maximum outer diameter.

16. The anchoring fixture of claim 15, wherein:
the threaded body includes a threaded section including the screw thread;
the anchoring fixture includes a non-threaded section distinct from the non-threaded body;
the non-threaded section is between the threaded section and the non-threaded body;
the non-threaded section has a minimum inner diameter that is greater than a minimum inner diameter of the threaded section; and
the non-threaded section includes a surface that flares outward from the minimum inner diameter of the non-threaded section at a constant angle towards a flat surface of the non-threaded body, which flat surface is normal to the longitudinal axis of the anchoring fixture.

17. The anchoring fixture of claim 15, wherein:
the threaded body includes a threaded section including the screw thread; and
a section between the non-threaded body and the threaded section includes a recessed portion that extends about the anchoring fixture at a constant location relative to location along the longitudinal axis of the anchoring fixture, the recessed portion being a portion of smallest diameter between the non-threaded body and the thread section, the recessed portion spanning a distance in a direction of the longitudinal axis a distance less than a pitch of the screw thread of the threaded section.

18. The anchoring fixture of claim 15, wherein:
the threaded body includes a threaded section;
the non-threaded body includes a flat surface that is normal to the longitudinal axis of the anchoring fixture; and
a cross section lying on and parallel to the longitudinal axis includes a portion, relative to direction along the longitudinal axis, between the threaded section and the flat surface, that includes a straight surface that extends away from the longitudinal axis at an oblique angle relative to the longitudinal axis.

19. The anchoring fixture of claim 15, wherein:
the screw thread extends in a downstream direction about the anchoring fixture from distal to proximal of the anchoring fixture, a distal end of the anchoring fixture being further from the non-threaded body than a proximal end of the anchoring fixture, the screw thread having a plurality of breaks along a length of the screw thread, respective breaks establishing respective self-tapping edges along the screw thread, the respective breaks being upstream from the respective self-tapping edges, wherein respective crests of the screw thread at the respective self-tapping edges are flat, and respective crests of the screw thread immediately upstream from the self-tapping edges across the respective breaks are also flat, and wherein respective widths of respective flats at the respective self-tapping edges are less than respective widths of respective flats of respective crests of the thread immediately upstream from the self-tapping edges.

20. The anchoring fixture of claim 1, wherein:
portions of the projection facing a distal end of the anchoring fixture have a compound surface.

21. The anchoring fixture of claim 1, wherein:
portions of the projection facing a distal end of the anchoring fixture include a first surface and a second surface extending from the first surface at an oblique angle.

22. The anchoring fixture of claim 1, wherein:
with respect to distance from the longitudinal axis, the projection has an outermost periphery, and portions of the projection inboard of the outermost periphery on a side of the projection facing a distal end of the anchoring fixture have surfaces that extend away from the longitudinal axis at different angles relative to one another.

23. The anchoring fixture of claim 1, wherein:
the projection is an annular projection about the longitudinal axis.

24. The anchoring fixture of claim 1, wherein:
the projection is a flange.

25. The anchoring fixture of claim 1, wherein:
the projection is a flange configured to function as a stop for the anchoring fixture adapted to rest on top of the skull bone when the anchoring fixture is implanted into the skull bone.

26. The anchoring fixture of claim 1, wherein:
the projection is a flange that has an outer profile that includes a portion that includes (i) a first surface that is parallel to the longitudinal axis of the anchoring fixture, (ii) a second surface that is normal to the longitudinal axis of the anchoring fixture, and (iii) a third surface that is located between the first surface and the second surface; and
the first surface establishes, relative to the longitudinal axis, an outermost portion of the flange, and wherein the second surface faces a distal end of the anchoring fixture.

27. The anchoring fixture of claim 1, wherein:
the projection includes a first surface that is part of a bottom of the projection;
the first surface is a planar surface; and
wherein the bottom further includes a second surface that extends obliquely or curvedly away from the first surface.

28. The anchoring fixture of claim 1, wherein:
the anchoring fixture is configured so that the projection rests on top of the bone when the anchoring fixture is implanted into the bone.

29. The anchoring fixture of claim 2, wherein:
the means for preventing penetration includes a first surface and a second surface obliquely angled relative to the first surface, wherein the first surface and the second surface face the screw thread.

30. The anchoring fixture of claim 2, wherein:
the means for preventing penetration includes a first surface and a second surface curved or obliquely angled relative to the first surface, wherein at least the first surface faces the screw thread and is a planar surface, and wherein the second surface extends from the first surface to a third surface that is, relative to a longitudinal axis, an outermost surface of the anchoring fixture.

31. The anchoring fixture of claim 2, wherein:
a bottom face of the means for preventing penetration is established by at least a first planar surface extending normal to a longitudinal axis of the anchoring fixture and a second surface extending obliquely from the first planar surface.

32. The anchoring fixture of claim 2, wherein:
the anchoring fixture has a groove; and
a minimum inner diameter of the groove is greater than a maximum inner diameter of the screw thread and a maximum outer diameter of the groove is less than a maximum outer diameter of the screw thread.

33. The anchoring fixture of claim 2, further comprising:
means for exerting a compression onto the skull bone in a radial direction to stabilize the anchoring fixture in the skull bone.

34. The anchoring fixture of claim 15, further comprising:
means for exerting a compression onto the skull bone in a radial direction to stabilize the anchoring fixture in the skull bone.

35. The anchoring fixture of claim 2, further comprising:
a circumferential groove, wherein the circumferential groove is coaxial with the means for preventing penetration.

36. The anchoring fixture of claim 15, further comprising:
a circumferential groove, wherein the circumferential groove is coaxial with the non-threaded body.

37. The anchoring fixture of claim 15, wherein:
the non-threaded body is a flange.

38. The anchoring fixture of claim 15, wherein:
the anchoring fixture consists of the threaded body and the non-threaded body.

39. The anchoring fixture of claim 15, wherein:
the threaded body and the non-threaded body are part of a monolithic component.

40. The anchoring fixture of claim 15, wherein:
the non-threaded body is a screw head.

41. The anchoring fixture of claim 15, wherein:
the non-threaded body has a stop face facing the threaded body that has a plurality of surfaces obliquely angled relative to one another.

42. The anchoring fixture of claim 15, wherein:
the non-threaded body has a face that is on a first side of a plane that is normal to the longitudinal axis of the anchoring fixture, which first side faces a distal end of the anchoring fixture, the face being a compound face.

43. The anchoring fixture of claim 15, wherein:
the non-threaded body has a side that is on a first side of a plane that is normal to the longitudinal axis of the anchoring fixture, which first side faces a distal end of the anchoring fixture, the side being established by a plurality of surfaces that are obliquely angled relative to one another.

44. The anchoring fixture of claim 43, wherein:
the plurality of surfaces includes a surface that is planar and a surface that is non-planar.

45. The anchoring fixture of claim 43, wherein:
the plurality of surfaces includes a surface that is planar and a surface that is oblique relative to the surface that is planar.

46. The anchoring fixture of claim 2, wherein the anchoring fixture has a circumferential groove that extends around a periphery of a cylindrical portion of the anchoring fixture.

47. The anchoring fixture of claim 46, wherein:
the circumferential groove is located, with respect to a side of the means for preventing penetration, on a threaded side of the anchoring fixture.

48. The anchoring fixture of claim 46, wherein:
the circumferential groove extends completely around a periphery of the main body.

49. The anchoring fixture of claim 46, wherein:
the circumferential groove extends partly around a periphery of the main body.

50. The anchoring fixture of claim 1, further comprising:
a circumferential groove, wherein the circumferential groove is separate from the screw thread of the main body.

51. The anchoring fixture of claim 2, wherein:
the anchoring fixture has a first section, with respect to location along a longitudinal axis of the anchoring fixture, between a surface of the means for preventing penetration that extends normal to the longitudinal axis and is configured to abut a top surface of the skull bone and at least a portion of the screw thread;
the first section is a grooved section; and
at least one of:
the first section overlaps with the threaded section; or
the first section blends into the screw thread.

52. The anchoring fixture of claim 2, wherein:
the anchoring fixture has a first section, with respect to location along a longitudinal axis of the anchoring fixture, between a surface of the means for preventing penetration that extends normal to the longitudinal axis and is configured to abut a top surface of the skull bone and at least a portion of the screw thread;
the first section is a grooved section; and
there is no distinct region separating the first section from the screw thread.

53. The anchoring fixture of claim 1, wherein:
the screw thread includes an inner diameter that remains about constant over at least about two turns of the screw thread.

54. The anchoring fixture of claim 2, wherein:
the anchoring fixture has an area having a diameter that is greater than the maximum inner diameter of the screw thread, the area being configured to exert a compression force onto the skull bone in a radial direction, thereby stabilizing the anchoring fixture in the skull bone when implanted therein.

55. The anchoring fixture of claim 2, wherein the maximum diameter of the screw thread is between 3.5 mm and 5 mm.

56. The anchoring fixture of claim 15, wherein:
the threaded body has a first section where a maximum thread outer radius as measured from the longitudinal axis of the anchoring fixture is less than that of a second section of the threaded body;
the second section is located closer to a distal end of the anchoring fixture than the first section;
the non-threaded body is located between a proximal end of the anchoring fixture and the distal end; and
a crest of the screw thread of the first section is non-contiguous with a crest of the screw thread of the second section.

57. The anchoring fixture of claim 1, wherein:
the anchoring fixture includes a group of respective self-tapping cutting edges on the screw thread established at least by respective breaks in the screw thread, the group being aligned in a longitudinal direction of the anchoring fixture;
respective crests of the screw thread at the cutting edges of the group are flat; and
respective crests of the screw thread at the respective breaks opposite the respective cutting edges are respectively flat and have respective flat distances that are longer in the longitudinal direction than respective flat distances of the cutting edges.

58. The anchoring fixture of claim 15, wherein:
the non-threaded body includes a flat surface that is normal to the longitudinal axis of the anchoring fixture and which faces the threaded body; and
a section of the anchoring fixture, relative to direction along the longitudinal axis, between a threaded section of the threaded body and the flat surface, includes a conical surface that extends away from the longitudinal axis at an oblique angle relative to the longitudinal axis.

59. The anchoring fixture of claim 15, wherein:
the non-threaded body includes a flat surface that is normal to the longitudinal axis of the anchoring fixture and which faces the threaded body; and
a cross section of the anchoring fixture lying on and parallel to the longitudinal axis includes a portion, relative to direction along the longitudinal axis, between a threaded section of the threaded body and the flat surface, that includes a first straight surface that extends away from the longitudinal axis at an oblique angle relative to the longitudinal axis, and
the portion relative to direction along the longitudinal axis, between the threaded section and the flat surface, includes a second surface that extends away from an outermost boundary of the first straight surface and overall, is parallel to the longitudinal axis.

60. The anchoring fixture of claim 1, wherein:
the anchoring fixture has a first section, with respect to location along the longitudinal axis of the fixture, between a surface of the projection that extends normal to the longitudinal axis and is configured to abut a top surface of the skull bone and at least a portion of the screw thread; and
the first section has a cross-section lying on the longitudinal axis and parallel to the longitudinal axis that has a V shape opening away from the longitudinal axis.

61. The anchoring fixture of claim 15, wherein the anchoring fixture is configured to exert a compression onto the skull bone in a radial direction, to stabilize the anchoring fixture in the skull bone, when the anchoring fixture is implanted.

62. The anchoring fixture of claim 1, wherein:
with respect to a cross-section of the anchoring fixture lying on and parallel to the longitudinal axis of the anchoring fixture, the anchoring fixture has, on one side, with respect to a direction from a proximal end of the anchoring fixture towards a distal end of the anchoring fixture along the tapered portion, crests of screw thread of the tapered portion that are all flat, and, on an opposite side from the one side, a crest of screw thread that is sharp.

63. The anchoring fixture of claim 2, wherein:
a cross-section of the anchoring fixture lying on and parallel to a longitudinal axis of the anchoring fixture has, on one side, with respect to location from a proximal end of the anchoring fixture to a distal end of the anchoring fixture, starting at a location of maximum screw thread radius on the one side, six turns inclusive of the turn having the maximum screw thread radius.

64. The anchoring fixture of claim 2, wherein:
the anchoring fixture is tapered over at least a portion of a longitudinal length of the anchoring fixture.

* * * * *